US Patent Number: 4,880,825
Date of Patent: Nov. 14, 1989

Kasai et al.

[54] MITOMYCIN DERIVATIVES

[75] Inventors: Masaji Kasai, Kanagawa; Yutaka Kanda, Tokyo; Motomichi Kono, Tokyo; Yutaka Saito, Tokyo; Makoto Morimoto; Tadashi Ashizawa, both of Shizuoka, all of Japan

[73] Assignee: Kyowa Hakko Kogyo Kabushiki Kaisha, Tokyo, Japan

[21] Appl. No.: 173,219

[22] Filed: Mar. 25, 1988

[30] Foreign Application Priority Data

Mar. 25, 1987 [JP] Japan .................. 62-71115

[51] Int. Cl.$^4$ ............... C07D 487/14; A61L 31/40
[52] U.S. Cl. ................. 514/409; 548/422; 548/407
[58] Field of Search .......... 548/422, 407; 514/410, 514/409

[56] References Cited

U.S. PATENT DOCUMENTS 3,226,393  12/1965  Meyer et al. .................. 260/295

FOREIGN PATENT DOCUMENTS

P22379   3/1967  Japan .
A122797  9/1979  Japan .
A15408   2/1980  Japan .
A45322   3/1980  Japan .
A118396  9/1980  Japan .
A7787    1/1981  Japan .
A30798   3/1981  Japan .
P21993   5/1985  Japan .
A68489   4/1986  Japan .
A91189   5/1986  Japan .

OTHER PUBLICATIONS

Merck Index, 10th Edition (1983).
Tetrahedron Letters, 26, 3923–3926 (1985).
Journal of Antibiotics, 33, 804–809 (1980).

Primary Examiner—Nicholas S. Rizzo
Attorney, Agent, or Firm—Wolder, Gross & Yavner

[57] ABSTRACT

Mitomycin derivatives having potent anti-tumor activity having the formula:

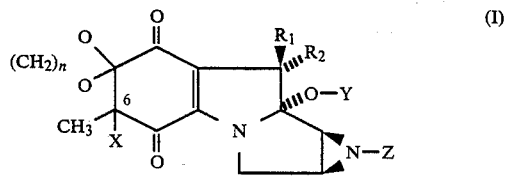

wherein one of $R_1$ and $R_2$ represents carbamoyloxymethyl and the other represents hydrogen or $R_1$ and $R_2$ are bonded together to form methylene;
X is hydrogen or halogen;
Y is hydrogen or methyl;
Z is hydrogen, methyl or acyl; and
n is an integer of 2 or 3.

7 Claims, No Drawings

MITOMYCIN DERIVATIVES

The present invention relates to mitomycin derivatives having anti-bacterial and anti-tumour activities.

Mitomycins, in general, are known to exhibit anti-bacterial and anti-tumour activities. Mitomycins originating from naturally-occurring substances are typically exemplified by mitomycin C and, found only in trace amounts, mitomycin A, mitomycin B and porfiromycin (disclosed in the Merck Index, 10th Edition). Further examples of characterised mitomycins include mitomycin D and mitomycin E (disclosed in JP-A-122797/79), mitomycin F and mitomycin J (disclosed in JP-A-45322/80) and mitomycin G, mitomycin H and mitomycin K (disclosed in JP-A-118396/80). The structures of the above-mentioned mitomycins originating from naturally-occurring substances are shown in the following Table 1.

TABLE 1
Structures of naturally-occurring mitomycins

| MM* | $X_A$ | $Y_A$ | $Z_A$ | $R_A$ | $R_B$ |
|---|---|---|---|---|---|
| A | $OCH_3$ | $CH_3$ | H | $CH_2OCONH_2$ | H |
| B | $OCH_3$ | H | $CH_3$ | H | $CH_2OCONH_2$ |
| C | $NH_2$ | $CH_3$ | H | $CH_2OCONH_2$ | H |
| D | $NH_2$ | H | $CH_3$ | H | $CH_2OCONH_2$ |
| E | $NH_2$ | $CH_3$ | $CH_3$ | H | $CH_2OCONH_2$ |
| F | $OCH_3$ | $CH_3$ | $CH_3$ | $CH_2OCONH_2$ | H |
| G | $NH_2$ | $CH_3$ | $CH_3$ | bonded together | ($=CH_2$) |
| H | $OCH_3$ | H | $CH_3$ | bonded together | ($=CH_2$) |
| J | $OCH_3$ | $CH_3$ | $CH_3$ | H | $CH_2OCONH_2$ |
| K | $OCH_3$ | $CH_3$ | $CH_3$ | bonded together | ($=CH_2$) |
| P** | $NH_2$ | $CH_3$ | $CH_3$ | $CH_2OCONH_2$ | H |

(MM* mitomycin; P** porfiromycin)

Various other mitomycins, which cannot be obtained directly from naturally-occurring substances, can be synthesized. These synthetic mitomycins are exemplified by 9a-0-demethylmitomycin G (disclosed in JP-A-15408/80), 1a-demethylmitomycin G and 1a-demethylmitomycin K (disclosed in JP-A-7787/81) and 9-epimitomycin B and 9-epi-mitomycin D (disclosed in JP-A-30978/81), the structures of which are shown in Table 2.

TABLE 2
Structures of synthetic mitomycins

| MM | $X_A$ | $Y_A$ | $Z_A$ | $R_A$ | $R_B$ |
|---|---|---|---|---|---|
| 9a-0-demethylMG | $NH_2$ | H | $CH_3$ | bonded together | ($=CH_2$) |
| 1a-demethylMG | $NH_2$ | $CH_3$ | H | bonded together | ($=CH_2$) |
| 1a-demethylMK | $OCH_3$ | $CH_3$ | H | bonded together | ($=CH_2$) |

TABLE 2-continued
Structures of synthetic mitomycins

| MM | $X_A$ | $Y_A$ | $Z_A$ | $R_A$ | $R_B$ |
|---|---|---|---|---|---|
| 9-epiMB | $OCH_3$ | H | $CH_3$ | $CH_2OCONH_2$ | H |
| 9-epiMD | $NH_2$ | H | $CH_3$ | $CH_2OCONH_2$ | H |

Notes:
MM — mitomycin:
MG — mitomycin G;
MK — mitomycin K;
MB — mitomycin B;
MD — mitomycin D The above-mentioned mitomycins includes some having excellent anti-tumour activity which have, however, certain undesirable side effects such as causing a decrease in the number of leucocytes. Thus, attempts have been made to prepare, synthetically, mitomycin derivatives having higher activity or reduced toxicity.

Known compounds in which the carbon atom at the 6th position of the quinone portion of the mitomycin skeleton carries no double bond, include, for example, compounds of the following formula (II):

(II)

The compounds of formula (II), in which R is methyl, ethyl, aryl or benzyl are disclosed in Tetrahedron Letters, 26, 3923–3926 (1985), and the compound carrying as R an ethyl group is disclosed in Example 2 of JP-A-91189/86.

Mitomycin C is known as an excellent chemotherapeutic agent for treating cancer and is widely used for clinical purposes in Japan and various other countries. However, mitomycin C has certain significant side effects such as its toxicity to bone marrow. Thus, it has been desired to provide agents having higher anti-tumour activity and/or reduced toxicity.

As a result of our research into mitomycin derivatives having improved properties, it has been found that a novel class of (6-halo-)7-polymethylenedioxymitomycins exhibit excellent anti-bacterial and anti-tumour activities. Mitomycin derivatives containing a spiro substituent of this type are believed to be structurally unique and moreover exhibit very interesting activity in comparison with the above-mentioned known derivatives.

The present invention thus provides mitomycin derivatives having excellent anti-tumour activity of the following formula:

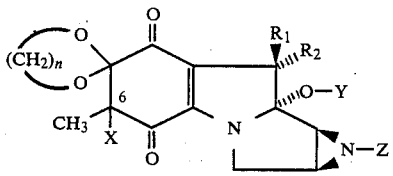

(I)

wherein one of $R_1$ and $R_2$ represents carbamoyloxymethyl and the other represents hydrogen or $R_1$ and $R_2$ are bonded together to form methylene;

X is hydrogen or halogen;

Y is hydrogen or methyl;

Z is hydrogen, methyl or acyl; and n is an integer of 2 or 3.

Hereinafter, the compounds of formula (I) are referred to as Compounds I.

With regard to the definition of X in formula (I), halogen is exemplified by chlorine, bromine and iodine.

With regard to the definition of Z, R of the acyl group (RCO) is preferably hydrogen, alkyl (preferably lower alkanoyl having 1–4 carbon atoms, for example, formyl, acetyl, propionyl and butyryl) or unsubstituted or substituted aryl (for example, benzoyl, p-nitrobenzoyl and naphthoyl).

Compounds I may be prepared by the following processes:

Process 1

Synthesis of Compound I-1 (Compound I wherein X=hydroqen)

Synthesis of Compound I-1 may be effected by the reaction of a mitomycin derivative having alkoxy at the 7th position with ethylene glycol or 1,3-propanediol in the presence of a base which is used as a catalyst. Similar reaction conditions are known in the processes used for the substitution at the 7th position of alkoxy mitomycin derivatives by another alkoxy at the 7th position (disclosed in Japanese Patent Publication 21993/85; The Journal of Antibiotics, 33, 804–809 (1980); JP-A-68489/86 and the like).

It is preferred to use 7-methoxymitomycins as the alkoxy mitomycin derivatives. Examples of 7-methoxymitomycins include those shown in Tables 1 and 2 such as mitomycin A, mitomycin B, mitomycin F, mitomycin H, mitomycin J, mitomycin K, 1a-demethylmitomycin K, 9-epi-mitomycin B, 7-methoxy-1a-acylmitomycins etc. Examples of 7-methoxy-1a-acylmitomycins include those shown in Tables 1 and 2, wherein $X_A$ represents methoxy and $Z_A$ represents acyl. They are exemplified by 1a-benzoylmitomycin A etc. (disclosed in U.S. Pat. No. 3,226,393 and Japanese Patent Publication 22379/67).

For carrying out the reaction, any and all solvents may be used provided they can dissolve the mitomycin used as raw material. Examples of the preferred solvents include dimethylformamide, dimethyl sulfoxide, tetrahydrofuran, methylene chloride and chloroform. If desired, it is also possible to use as the solvent, for example, an excess of ethylene glycol or 1,3-propanediol used for the reaction.

Examples of the bases used for the reaction include ROM (wherein R is a lower alkyl having 1–4 carbon atoms and M is selected from alkali metals and alkaline earth metals), $MO(CH_2)_nOM$ (wherein M is as hereinbefore defined and n is an integer of 2 or 3), hydroxides, carbonates or bicarbonates of both alkali metals and alkaline earth metals, tertiary amines and quaternary ammonium hydroxide.

0.001–10 (preferably 0.01–3) moles of base may e.g. be used per mole of mitomycin. The reaction may be effected e.g. at a temperature within a range of −20 to 70° C. (preferably 10°–30° C.) and completed in a period of for example 2 to 24 hours. Completion of the reaction may readily be detected by silica gel thin layer chromatography. After this, the reaction solution is neutralized, for example, with organic acid such as acetic acid or propionic acid, inorganic acid such as hydrochloric acid or sulphuric acid; or dry ice. The reaction product is extracted with a water-insoluble solvent for example, chloroform, methylene chloride or ethyl acetate, and washed with water or a saturated saline solution or the like. The extracted solution is concentrated and purified, for example, by column chromatography, TLC, recrystallization and the like.

Alternatively, Compound I-1 (wherein Z is acyl) may be produced by the reaction of Compound I-1 (wherein Z is hydrogen) with an acylating agent in the presence of a base in an inert solvent. The acylating agents which may be used include the corresponding acid anhydrides and acid halides and are exemplified by acetic anhydride and benzoyl chloride. Preferred bases are exemplified by organic base such as pyridine and triethylamine. Examples of the preferred solvents include methylene chloride or chloroform although it is possible, if desired, to use pyridine as the solvent.

Process 2

Synthesis of Compound I-2 (Compound I wherein X=halogen)

Synthesis of Compound I-2 (wherein Z=methyl or acyl) may be effected by the reaction of a Compound I-1 obtained by Process 1 (wherein Z=methyl or acyl) with a suitable halogenating agent in the presence of a base.

Compounds which may be preferred for this reaction are exemplified by mitomycins such as 1a-acetyl-7-demethoxy-6,7-dihydro-7-ethylenedioxymitomycin A, 7-demethoxy-6,7-dihydro-7-ethylenedioxymitomycin B and 7-demethoxy-6,7-dihydro-7-ethylenedioxymitomycin F.

Any and all solvents capable of dissolving the mitomycins used as raw materials for example, dimethylformamide, tetrahydrofuran, chloroform or methylene chloride may be used for the reaction either alone or in admixture.

The bases which may be preferred for the reaction include, for example, organic bases such as triethylamine or pyridine. It is possible to use the base in a greater than equimolar ratio, preferably 4–10 moles of base per mole of Compound I-1, although in some cases (depending on the type of halogenating agent used) it is not necessary to use the base.

The halogenating agents which may usually be used for the reaction include, for example, N-chlorosuccinimide and N-bromosuccinimide. Usually, the reaction may be completed in a period of 40 minutes to 12 hours at a temperature of 0° to 30° C. After this, a buffer solution may be employed to neutralize the reaction mixture. The reaction mixture is extracted with a water-immiscible solvent such as chloroform, methylene chloride or ethyl acetate. After washing, for example, with water or a saturated saline solution, the extracted solution is concentrated and purified. The purification may be effected, for example, by column chromatography, TLC and recrystallization.

Compound I-2 (wherein Z is hydrogen) may be prepared by treating a Compound I-2 (wherein Z=acyl for example, acetyl) with a base. The bases which may be used for this reaction may be, for example, an amine or ammonia, or an inorganic base such as sodium bicarbonate. The use of, for example, methanol and water as solvent is preferred. The reaction may be completed in a period of 10–20 hours. After after-treatment in conventional manner, the desired product may be purified, for example, by silica gel column chromatography.

Compounds I may be used as anti-tumour agents, if desired, in association with at least one pharmaceutically acceptable diluent, adjuvant and/or carrier. The anti-tumour composition may comprise, if desired, well-recognized diluents, for example, Ringer's solution, adjuvants, for example, polyethylene glycol, HCO-60 (surfactant: commercial product of Nikko Chemicals K.K., Japan), ethanol and/or carriers, for example, liposome, cyclodextrin and the like.

The compounds may usually be formulated into an injection agent by dissolving in physiological saline solution or an injection solution of glucose, lactose or mannitol. However, the composition may also take the form of tablets, powders, granules, syrups or suppositories. Each compound may be administered to mammals, in particular to humans, at a dose of 0.06 to 5 mg/kg. The administration may usually be effected intravenously using an injection agent prepared by dissolving Compound I, for example, in a physiological saline solution or a solution of glucose or fructose for injection. It is also possible to administer the compound at a similar dose into an artery, the abdominal cavity or the thorax. If desired, the compounds may be freeze-dried with reference to the Pharmacopoeia of Japan or may be formulated into injection powders containing sodium chloride.

The dose of the compound may vary, depending upon the age and symptoms of each patient, and the administration schedule may also be variable depending upon the symptoms and the dosage administered. Thus, it is possible to administer the compound intermittently, for example, once per week or once per three weeks. A similar dose may be administered by oral or rectal route.

Our invention is illustrated in the following Examples and Experiments in which the physico-chemical characteristics of the compounds were determined by means of the following instruments:

Melting point: Apparatus for measuring micro melting point (using without modification the commercially available apparatus of Yanagimoto, Japan)

$^1$H-NMR: Bruker AM400 (400 MHz) or Varian EM390 (90 MHz) (measured in deutero chloroform)

MS: M-80B (Hitachi Ltd., Japan; measured by the SI method)

IR: IR-810 (Nihon Bunko K.K., Japan; measured by the KBr method)

Table 3 indicates the structures of typical Compounds 1 obtained by synthesis:

TABLE 3

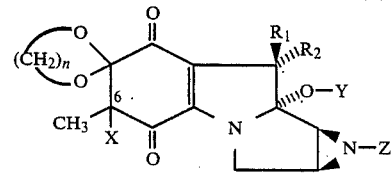

(I)

| Compound No. (Example No.) | $R_1$ | $R_2$ | X | Y | Z | n |
|---|---|---|---|---|---|---|
| 1 (1) | CH$_2$OCONH$_2$ | H | H | CH$_3$ | H | 2 |
| 2 (2) | H | CH$_2$OCONH$_2$ | H | H | CH$_3$ | 2 |
| 3 (3) | CH$_2$OCONH$_2$ | H | H | CH$_3$ | CH$_3$ | 2 |
| 4 (4) | H | CH$_2$OCONH$_2$ | H | CH$_3$ | CH$_3$ | 2 |
| 5 (5) | bonded together | (=CH$_2$) | H | H | CH$_3$ | 2 |
| 6 (6) | CH$_2$OCONH$_2$ | H | H | CH$_3$ | H | 3 |
| 7 (7,8) | CH$_2$OCONH$_2$ | H | H | CH$_3$ | COCH$_3$ | 2 |
| 8 (9) | CH$_2$OCONH$_2$ | H | Cl | CH$_3$ | H | 2 |
| 9 (10) | H | CH$_2$OCONH$_2$ | Cl | H | CH$_3$ | 2 |
| 10 (11) | CH$_2$OCONH$_2$ | H | Br | CH$_3$ | CH$_3$ | 2 |
| 11 (12) | CH$_2$OCONH$_2$ | H | Cl | CH$_3$ | COCH$_3$ | 2 |

EXAMPLE 1

7-demethoxy-6,7-dihydro-7-ethylenedioxymitomycin A (Compound 1)

Mitomycin A (1.0 g) was dissolved in a mixture of tetrahydrofuran (15 ml) and ethylene glycol (3 ml). After addition of an ethylene glycol solution (0.5 ml) containing 1.6% (w/w) of potassium hydroxide, the mixture was stirred at a temperature of 25° C. for 5 hours. Then, an excess of dry ice, in small pieces, was added to the reaction solution while stirring. The reaction solution was diluted with chloroform. The organic layer was washed with a saturated saline solution and dried using anhydrous sodium sulphate. The drying agent was removed by filtration and the solvent was evaporated under reduced pressure. The residue was subjected to silica gel column chromatography using a solvent system of chloroform/methanol (97:3 v/v). The eluted yellowish-orange fractions were collected, from which the solvent was removed by evaporation under reduced pressure. The residue was dissolved in a small amount of chloroform. n-hexane was added thereto to obtain powders which were then evaporated under reduced pressure to remove the solvent. By drying the material well at a temperature of 25° C. in vacuo, 880 mg of Compound 1 was obtained in the form of yellowish-orange powders at a yield of 81%. By subjecting this compound to TLC using silica gel (Art. 5719, commercial product of Merck AG., West Germany) and a solvent system of chloroform/ methanol (9:1 v/v), an Rf value of 0.27 was observed.

Melting point: 165–168° C. (decomp.)

MS: m/z 380 (M$^+$+1) C17H21N3O7=379

IR: cm$^{-1}$ 3446, 3296, 2902, 1727, 1702, 1642, 1575, 1447, 1336, 1186, 1068, 964, 855, 757, 705 NMR: δ, ppm (400MHz) ~0.9 (1H, bs), 1.18 (3H, d, J=6.6), 2.80 (1H, bs), 2.91 (1H, d, J=4.2),
3.21 (3H,s), 3.27 (1H, q, J=6.6), 3.44 (1H, dd, J=12.3, 1.5), 3.62 (1H, dd, J=10.6, 4.4), 3.83 (1H, d, J=12.8), 3.98~4.13 (3H, m), 4.39 (1H, m), 4.58 (1H, t, J=10.6), 4.78 (1H, dd, J=10.6, 4.4), 4.80 (2H, bs).

EXAMPLE 2

7-demethoxy-6,7-dihydro-7-ethylenedioxymitomycin B (Compound 2)

In a similar manner to that described in Example 1, mitomycin B (230 mg), ethylene glycol (7.2 ml) and an ethylene glycol solution (0.5 ml) containing 1.6% (w/w) of potassium hydroxide (hereinafter referred to as KOH solution) were treated to give Compound 2 (125 mg) in the form of yellow powders at a yield of 50%.

It was found that the resultant Compound 2 was a mixture of two compounds having different stereochemical structures at the C$_6$-position (diastereoisomers) and which respectively showed Rf values of 0.41 and 0.47 when subjected to TLC using silica gel (Art. 5719, commercial product of Merck AG., West Germany) developed using a solvent system of chloroform/methanol (9:1 v/v). The ratio of the two compounds was about 4:1 on the basis of NMR data. Hereinafter, the ratio is expressed similarly.

Melting point: 165°-170° C. (decomp. with colour change)
MS: m/z 380 (M$^+$+1) $C_{17}H_{21}N_3O_7$ =379
IR: cm$^{-1}$ 3450, 2960, 2900, 1718, 1702, 1640, 1570, 1445, 1340, 1204, 1063, 951, 847, 705
NMR: δ, ppm (400 MHz)
Major: 1.18 (3H, d, J=6.6), 2.23 (3H, s), 2.23 (1H, dd, J=4.4, 2.0), 2.26 (1H, d, J=4.4), 3.23 (1H, q, J=6.6), 3.38 (1H, dd, J=12.8, 2.0), 3.72 (1H, d, J=12.8), 3.75 (1H, dd, J=5.7, 2.0), 3.95~4.15 (3H, m), 4.40 (1H, m), 4.47 (1H, s), 4.67 (1H, dd, J=11.6, 2.0), 4.73 (1H, dd, J=11.6, 5.7), ~4.7 (2H, bs)
Minor (main peaks): 1.25 (3H, d, J=7.1), 2.98 (1H, q, J=7.1), 3.33 (1H, bd, J=12.3), 3.93 (1H, d, J=12.6)

EXAMPLE 3

7-demethoxy-6,7-dihydro-7-ethylenedioxymitomycin F (Compound 3)

In a similar manner to that described in Example 1, Compound 3 (172 mg) in the form of yellow powders was obtained at a yield of 79% from mitomycin F (200 mg), tetrahydrofuran (2 ml), ethylene glycol (3 ml) and KOH solution (0.5 ml).

It was found that Compound 3 was a mixture of two compounds having different stereochemical structures at the C$_6$-position (diastereoisomers) and which respectively showed Rf values of 0.57 and 0.65 when subjected to silica gel TLC carried out under the same conditions as the conditions described in Example 2, the ratio of the two compounds being about 4:1.

Melting point: 88°-92° C.
Melting point: m/z 394 (M$^+$+1) $C_{18}H_{23}N_3O_7$ =393
IR: cm$^{-1}$ 3420, 2938, 2900, 1720, 1708, 1650, 1576, 1449, 1340, 1203, 1056, 1031, 972, 950, 846
NMR: δ, ppm (400 MHz)
Major:1.18 (3H, d, J=6.6), 2.22 (1H, dd, J=4.7, 2.2), 2.25 (3H, s), 2.29 (1H, d, J=4.7), 3.18 (3H, 3.27 (1H, q, J=6.6), 3.39 (1H, dd, J=12.6, 2.2), 3.58 (1H, dd, J=10.6, 4.4), 3.80 (1H, d, J=12.6), 3.95 ~4.4 (4H, m), 4.40 (1H, t, J=10.6), 4.72 (2H, bs), 4.78 (1H, dd, J=10.6, 4.4)
Minor (main peaks): 1.25 (3H, d, J=6.9), 3.01 (1H, q, J=6.9), 3.19 (3H, s), 3.34 (1H, dd, J=12.3, 2.2), 4.70 (1H, dd, J=10.6, 4.4).

EXAMPLE 4

7-demethoxy-6,7-dihydro-7-ethylenedioxymitomycin J (Compound 4)

In a similar manner to that described in Example 1, Compound 4 (151 mg) in the form of yellow powders was obtained from mitomycin J (160 mg), tetrahydrofuran (1 ml), ethylene glycol (2 ml) and KOH solution (0.3 ml) at a yield of 87%.

It was found that Compound 3 was a mixture of two compounds having different stereochemical structures at the C$_6$-position (diastereoisomers) and which respectively showed Rf values of 0.56 and 0.58 when subjected to silica gel TLC carried out under the same conditions as the conditions described in Example 2, the ratio of the two compounds being about 3:1.

Melting point: 83°-87° C. (decomp.)
MS: m/z 394 (M$^+$+1) $C_{18}H_{23}N_3O_7$=393
IR: cm$^{-1}$ 3470, 3370, 2952, 2900, 1715, 1655, 1577, 1461, 1335, 1275, 1200, 1111, 1075, 942, 843, 706
NMR: δ, ppm (400 MHz)
Major: 1.19 (3H, d, J=6.6), 2.23 (1H, d, J=4.7), 2.30 (3H, s), 2.35 (1H, dd, J=4.7, 2.2), 3.17 (1H, q, J=6.6), 3.30 (3H, s), 3.51 (1H, dd, J=12.6, 2.2), 3.64 (1H, d, J=12.6), 3.91 (1H, dd, J=8.9, 3.9), 3.9~4.4 (4H, m), 4.48 (1H, dd, J=10.6, 9.1), 4.66 (2H, bs), 4.72 (1H, dd, J=10.8, 3.9)
Minor (main peaks): 1.23 (3H, d, J=7.1), 2.19 (1H, d, J=4.7), 2.29 (3H, s), 3.02 (1H, q, J=7.1), 3.30 (3H, s), 3.47 (1H, dd, J=12.6, 2.2), 3.82 (1H, d, J=12.6), 4.47 (1H, dd, J=10.8, 9.1), 4.77 (1H, dd, J=10.8, 3.9).

EXAMPLE 5

7-demethoxy-6,7-dihydro-7-ethylenedioxymitomycin H (Compound 5)

In a similar manner to that described in Example 1, Compound 5 (91 mg) in the form of yellowish-brown powders was obtained from mitomycin H (127 mg), tetrahydrofuran (1 ml), ethylene glycol (1.5 ml) and KOH solution (0.3 ml) in a yield of 65%.

It was found that Compound 5 was a mixture of two compounds having different stereochemical structures at the C$_6$-position (diastereoisomers) and which respectively showed Rf values of 0.64 and 0.65 when subjected to silica gel TLC carried out under the same conditions as the conditions described in Example 2, the ratio of the two compounds being about 3:1.

Melting point: 170°-175° C. (decomp.)
MS: m/z 319 (M$^+$+1) $C_{16}H_{18}N_2O_5$ =318
IR: cm$^{-}$3200, 2956, 2892, 1701, 1662, 1542, 1438, 1359, 1202, 1175, 1113, 1075, 1051, 950, 913, 846, 701, 632
NMR: δ, ppm (400 MHz)
Major: 1.19 (3H, d, J=6.6), 2.19 (3H, s), 2.25 (1H, dd, J=4.4, 1.7), 2.29 (1H, d, J=4.7), 2.78 (1H, bs), 3.30 (1H, q, J=6.6), 3.45 (1H, dd, J=12.8, 1.7), 3.82 (1H, d, J=12.8), 3.98~4.4 (4H, m), 5.67 (1H, s), 634 (1H, s)
Minor (main peaks): 1.27 (3H, d, J=7.1), 2.19 (3H, s), 2.97 (1H, q, J=7.1), 3.39 (1H, dd, J=12.3, 1.7), 4.02 (1H, d, J=12.3), 6.33 (1H, s).

EXAMPLE 6

7-demethoxy-6,7-dihydro-7-propylenedioxymitomycin A (Compound 6)

In a similar manner to that described in Example 1, Compound 6 (13 mg) in the form of yellowish-brown powders was obtained from mitomycin A (240 mg), tetrahydrofuran (2 ml), 1,3-propanediol (2 ml) and KOH (20 mg) in a yield of 5%.

It was found that Compound 6 showed Rf=0.45 when subjected to silica gel TLC carried out in a similar manner to that described in Example 2.

Melting point: 178°–183° C. (decomp.)

MS: m/z 394 (M++1) $C_{18}H_{23}N_3O_7$ =393

IR: $cm^{-1}$ 3430, 3308, 2956, 1725, 1701, 1649, 1573, 1464, 1446, 1329, 1191, 1164, 1099, 1040, 965, 858, 706

NMR: δ, ppm (400 MHz) ~ ~0.6 (1H, bs), 1.24 (3H, d, J=6.6), 1.43 (1H, bd, J=13.3), 2.02 (1H, m), 2.79 (1H, bd, J=3.9), 2.89 (1H, bd, J=3.9), 3.03 (1H, q, J=6.4), 3.21 (3H, s), 3.42 (1H, bd, J=12.3), 3.61 (1H, dd, J=10.6, 4.4), 3.82 (1H, bdd, J=9.4, 5.2), 3.85 (1H, d, J=12.3), 3.93 (1H, bdd, J=10.8, 5.2), 4.04 (1H, bt, J=12.8), 4.58 (1H, t, J=10.8), 4.72 (2H, bs), 4.83 (1H, dd, J=10.8, 4.4), 4.82 (1H, m).

EXAMPLE 7

1a-acetyl-7-demethoxy-6,7-dihydro-7-ethylenedioxymitomycin A (Compound 7)

In a similar manner to that described in Example 1, Compound 7 (120 mg) in the form of yellow powders was obtained from 1a-acetylmitomycin A (148 mg), tetrahydrofuran (3.5 ml), ethylene glycol (2 ml) and KOH solution (0.5 ml) in a yield of 75%.

It was found that Compound 7 was a mixture of two compounds having different stereochemical structures at the C6-position (diastereoisomers) and which showed the same Rf value of 0.52 when subjected to silica gel TLC carried out under the same conditions as the conditions described in Example 2, the ratio of the two compounds being about 2.5:1.

Melting point: 87°–92° C.

MS: m/z 422 (M++1) $C_{19}H_{23}N_3O_8$ =421

IR: $cm^{-1}$ 3480, 3292, 2900, 1720, 1700, 1645, 1575, 1448, 1328, 1268, 1189, 1067, 1031, 949, 859, 749

NMR: δ, ppm (400 MHz)

Major: 1.20 (3H, d, J=6.6), 2.11 (3H, s), 3.21 (3H, s), 3.22 (1H, q, J=6.6), 3.23 (1H, dd, J=4.4, 2.0), 3.47 (1H, dd, J=13.1, 2.0), 3.50 (1H, d, J=4.4), 3.73 (1H, dd, J=10.8, 4.9), 4.04 (1H, d, J=13.1), 3.98 –4.41 (4H, m), 4.17 (1H, t, J=11.1), 4.82 (2H, bs), 4.98 (1H, dd, J=11.1, 4.9)

Minor (main peaks): 1.24 (3H, d, J=6.9), 2.11 (3H, s), 3.04 (1H, q, J=6.9), 3.22 (3H, s), 3.42 (1H, dd, J=13.0, 1.7), 4.34 (1H, d, J=13.0), 4.89 (1H, dd, J=10.8, 4.9).

EXAMPLE 8

1a-acetyl-7-demethoxy-6,7-dihydro-7-ethylenedioxymitomycin A (Compound 7), (another method)

7-demethoxy-6,7-dihydro-7-ethylenedioxymitomycin A (Compound 1; 52 mg) was dissolved in a mixture of chloroform (1.0 ml) and pyridine (0.5 ml). After addition of acetic anhydride (13 μl), the mixture was stirred at a temperature of 25° C. for one hour. Then methanol (1.0 ml) was added and the mixture was stirred for 10 minutes. After addition of toluene (2 ml), the solution was evaporated under reduced pressure to remove the solvent. The residue was subjected to silica gel column chromatography in a similar manner to that described in Example 2. Elution was effected using a solvent system of chloroform/methanol (96:4 v/v) to collect yellow fractions. After removal of the solvent by evaporation under reduced pressure, the material was treated in a similar manner to that described in Example 1 to obtain Compound 7 (53 mg) in the form of yellow powders in a yield of 95%. The physico-chemical characteristics of the resultant compound are described hereinbefore.

EXAMPLE 9

6-chloro-7-demethoxy-6,7-dihydro-7-ethylenedioxymitomycin A (Compound 8)

1a-acetyl-7-demethoxy-6,7-dihydro-7-ethylenedioxymitomycin A (Compound 7; 210 mg) was dissolved in tetrahydrofuran (5.0 ml). N-chlorosuccinimide (100 mg) and triethylamine (0.5 ml) were added thereto. The mixture was stirred at a temperature of 20° C. for 12 hours. The solution was neutralized with a phosphate-buffered solution (pH 4) and was then extracted with chloroform. The layer resulting from extraction with chloroform was washed with a saturated saline solution and dried using anhydrous sodium sulphate. After removal of the solvent by evaporation under reduced pressure, the residue was dissolved in methanol (10 ml) and a methanol solution (2.0 ml) of ammonia (6.8M) was added thereto. The mixture was stirred at a temperature of 20° C. for 10 hours, followed by concentration of the reaction mixture without any after-treatment. The residue was subjected to silica gel chromatography. Elution was effected using a solvent system of chloroform/methanol (96:4 v/v) to collect yellow fractions, from which the solvent was then removed by evaporation under reduced pressure. The reaction product was dissolved in a small amount of chloroform and was then powdered with addition of n-hexane. The solvent was removed from the powders by evaporation under reduced pressure, followed by drying well at a temperature of 25° C. in vacuo to result in Compound 8 (142 mg) in the form of yellow powders in a yield of 68%.

It was found that Compound 8 was a mixture of two compounds having different stereochemical structures at the C6-position (diastereoisomers) 15. and which respectively showed Rf values of 0.30 and 0.34 when subjected to silica gel TLC carried out under the same conditions as the conditions described in Example 2, the ratio of the two compounds being about 6:1.

MS: m/z 414 (M++1) $C_{17}H_{20}N_3O_7Cl$ =413.8

IR: $cm^{-1}$ 3380, 2904, 1709, 1653, 1572, 1447, 1378, 1335, 1208, 1057, 994, 948, 855, 822, 778, 755, 686

NMR: δ, ppm (400 MHz)

Major: 0.66 (1H, brs), 1.74 (3H, s), 2.82 (1H, brs), 2.90 (1H, brs), 3.23 (3H, s), 3.42 (1H, d, J=12.3), 3.67 (1H, dd, J=10.3, 4.7), 4.10 (1H, d, J=12.8), 4.13~4.27 (4H, m), 4.55 (1H, t, J=10.6), 4.70 (1H, dd, J=10.7, 4.7), 4.87 (2H, brs)

Minor (main peaks) 1.71 (3H, s), 3.23 (3H, s), 3.48 (1H, brd, J=12.0), 3.94 (1H, d, J=12.0).

EXAMPLE 10

6-chloro-7-demethoxy-6,7-dihydro-7-ethylenedioxymitomycin B (Compound 9):

In a similar manner to that described in Example 9, 7-demethoxy-6,7-dihydro-7-ethylenedioxymitomycin B (190 mg; Compound 2), tetrahydrofuran (4 ml), triethylamine (0.2 ml) and N-chlorosuccinimide (210 mg) were treated to obtain Compound 9 (172 mg) in the form of yellow powders in a yield of 58%.

It was found that Compound 9 was a mixture of two compounds having different stereochemical structures at the C6-position (diastereoisomers), both of which showed the same Rf value of 0.53 by silica gel TLC carried out under the same conditions as the conditions described in Example 2, the ratio of the two compounds being about 3:1.

MS: m/z 414 (M$^+$ +1) $C_{17}H_{20}N_3O_7Cl$=413.8

IR: cm$^{-1}$ 3420, 2950, 1705, 1650, 1562, 1450, 1407, 1340, 1205, 1041, 949, 840, 805, 680

NMR: δ, ppm (400 MHz)

Major: 1.76 (3H, s), 2.22 (3H, s), 2.23 (1H, dd, J=4.7, 1.5), 2.26 (1H, d, J=4.7), 3.35 (1H, dd, J=12.8, 1.5), 3.72 (1H, dd, J=5.7, 1.7), 3.91 (1H, d, J=12.8), 4.03~4.31 (4H, m), 4.66 (1H, dd, J=11.8, 5.7), 4.73 (1H, dd, J=11.8, 1.7), 4.81 (2H, brs)

Minor (main peaks) 1.69 (3H, s), 2.22 (3H, s), 3.72 (1H, d, J=12.3), 3.83 (1H, dd, J=5.8, 2.0), 4.98 (2H, brs).

EXAMPLE 11

6-bromo-7-demethoxy-6,7-dihydro-7-ethylenedioxymitomycin F (Compound 10):

7-demethoxy-6,7-dihydro-7-ethylenedioxymitomycin F (Compound 3; 207 mg) was dissolved in methylene chloride. After addition of N-bromosuccinimide (95 mg) at a temperature of 25° C., the mixture was stirred for 40 minutes. The reaction mixture was added to a saturated solution of sodium bicarbonate, followed by extraction with chloroform. The chloroform layer was washed with a saturated saline solution and dried using anhydrous sodium sulphate. The solvent was removed from the reaction mixture by evaporation under reduced pressure to give a residue. The residue was subjected to silica gel column chromatography. Elution was effected using a solvent system of chloroform/methanol (95:5 v/v). From the yellow fractions collected, the solvent was removed by evaporation under reduced pressure. The residue was dissolved in a small amount of chloroform and powdered by addition of n-hexane. The solvent was removed from the powders by evaporation under reduced pressure to obtain Compound 10 (30 mg) in the form of yellow powders in a yield of 12%.

Compound 10 exhibited a Rf value of 0.43 when subjected to silica gel TLC in a similar manner to that described in Example 2.

MS: m/z 473 (M$^+$ +2) C. $C_{18}H_{22}N_3O_7Br$ =472.3

NMR: δ, ppm (90 MHz)

Main peaks: 1.83 (3H, s), 2.26 (3H, s), 3.22 (3H, s), 4.80 (2H, brs).

EXAMPLE 12

1a-acetyl-6-chloro-7-demethoxy-6,7-dihydro-7-ethylenedioxymitomycin A (Compound 11)

1a-acetyl-7-demethoxy-6,7-dihydro-7-ethylenedioxymitomycin A (Compound 7; 50 mg) was dissolved in tetrahydrofuran (2.0 ml). After addition of triethylamine (0.1 ml) and N-chlorosuccinimide (22 mg), the mixture was stirred at a temperature of 25° C. for 1.5 hour. The reaction mixture was neutralized with a phosphate-buffered solution (pH 4), followed by extraction with chloroform. The chloroform layer was washed with a saturated saline solution chloride and dried using anhydrous sodium sulphate. The solvent was removed from the material by evaporation under reduced pressure. The residue was subjected to silica gel column chromatography. Elution was effected using a solvent system of chloroform/methanol (98:2 v/v) to collect yellow fractions, from which the solvent was then removed by evaporation under reduced pressure. The residue was dissolved in a small amount of chloroform and powdered with addition of n-hexane. After removal of the solvent by evaporation under reduced pressure, the material was well dried in vacuo at a temperature of 25° C. to obtain Compound 11 (54 mg) in the form of yellow powders in a yield of 99%. When subjected to TLC using silica gel in a similar manner to that described in Example 2, a value of Rf=0.53 was observed.

MS: m/z (M$^+$ +1) $C_{19}H_{22}N_3O_8Cl$=455.5

IR: cm$^-$3360, 2950, 1705, 1656, 1574, 1460, 1366, 1326, 1236, 1199, 1071, 992, 949, 861, 801, 780, 690

NMR: δ, ppm (90 MHz)

Main peaks: 1.72 (3H, s), 2.10 (3H, s), 3.20 (3H, s), 3.70 (1H, dd, J=10.5, 4.5), 4.80 (1H, dd, J=10.5, 4.5), 5.1 (2H, brs).

EXPERIMENT

Compound 4 (2 g) was dissolved in distilled water (1000 ml) and sterilized by filtration under pressure using a Millipore filter having a pore diameter of 0.22μ. The resultant sterilized was poured into brown vials in 1 ml aliquots such that each vial contained 2 mg of the compound. The vials were freeze-dried at a temperature of −50° C. for 2 hours. Primary drying was effected for 24 hours in vacuo (0.1 mmHg) at a shelf temperature of −10° C. After confirmation of the agreement between the shelf and vial temperatures, secondary drying was effected in vacuo (0.1 mmHg) for 4 hours at a shelf temperature of 30° C. to remove moisture content. On each occasion, a rubber plug was used to seal the vial.

In use, an injection solution is prepared by adding a sterilized physiological saline solution (5 ml) to each vial with vigorous stirring to dissolve the ingredient.

The anti-bacterial activity, anti-tumour activity and acute toxicity of selected Compounds I are disclosed in the following:

Anti-bacterial activity

The following Table 4 shows anti-bacterial activity of selected Compounds I against various microorganisms expressed by the minimum inhibitory concentration (μg/ml) detected by the agar dilution method at pH 7.0. In this table, the microorganisms are abbreviated as follows:

SF: Streptococcus faecalis ATCC 10541
SA: Staphylococcus aureus ATCC 6538P
PV: Proteus vulgaris ATCC 6897
KP: Klebsiella pneumoniae ATCC 10031.

TABLE 4

| Compound No. (Example No.) | | SF | SA | PV | KP |
|---|---|---|---|---|---|
| 1 | (1) | 0.078 | 0.039 | 0.0098 | 0.0049 |
| 2 | (2) | 2.6 | 2.5 | 0.63 | 1.3 |
| 3 | (3) | 0.31 | 0.31 | 0.63 | 0.31 |
| 4 | (4) | 0.31 | 0.63 | 0.63 | 0.31 |
| 8 | (9) | 1.3 | 0.039 | 1.3 | 0.039 |
| 9 | (10) | 10 | >40 | >40 | 5.0 |
| 10 | (11) | 2.5 | 0.63 | 5.0 | 5.0 |

(2) Anti-tumour activity against Leukemia P-388 and acute toxicity (a) Effects upon Leukemia P-388

P-388 ascites tumour was abdominally implanted into a mouse (DBA/2). 7 days after this, ascitic fluid was collected from the tumour-carrying mouse. The number of P-388 cells was counted to prepare a cell suspension containing $5 \times 10^6$ cells/ml using a sterilized physiological saline solution. 0.2 ml of the cell suspension containing $1 \times 10^6$ cells was abdominally implanted into each mouse of $CDF_1$ strain (body weight 20–25 g). 24 hours after this, a test compound was abdominally given once to each mouse of a group consisting of 6 mice and their survival was observed for 33 days. The effect of the test compound was evaluated with reference to the ILS % (Increased Life Span) (the ratio of the average survival days of the test animals to the average survival days of the control group of untreated animals). The following Table 5 indicates ILS* (the ratio of ILS % obtained using each of the test compounds to the corresponding ILS % obtained using mitomycin C as control under the same conditions).

(b) Acute toxicity

The test compound was abdominally administered once to ddy mice and their survival was observed for 14 days. From the death ratio of each test group of animals, acute toxicity ($LD_{50}$) was calculated by the "Behrens-Koerber" method. The results are shown in the following Table 5.

TABLE 5

| Compound No. | $LD_{50}$ (mg/kg) | ILS(%) | Dose, mg/kg | ILS* |
|---|---|---|---|---|
| 1 | 0.70 | 169 | 0.39 | 1.00 |
| 2 | 7.5 | 173 | 5 | 1.06 |
| 3 | 4.5 | 153 | 2.5 | 0.77 |
| 4 | 6.0 | 180 | 5 | 1.16 |
| 8 | 3.75 | >164 | 1.56 | >0.93 |
| 9 | 15 | 159 | 12.5 | 1.13 |

We claim:

1. Mitomycin compounds represented by the Formula

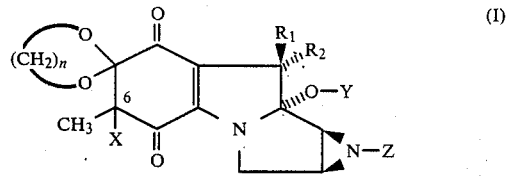

wherein one of $R_1$ and $R_2$ represents carbamoyloxymethyl and the other represents hydrogen or $R_1$ and $R_2$ are bonded together to form methylene;

X is hydrogen or halogen;

Y is hydrogen or methyl;

Z is hydrogen, methyl or acyl of the Formula RCO where R is selected from the group consisting of hydrogen, lower alkyl or 1 to 3 carbon atoms, phenyl, p-nitrophenyl and naphthyl; and n is an integer of 2 or 3.

2. Mitomycin compounds according to claim 1 wherein X is a member of the group consisting of chlorine, bromine and iodine.

3. Mitomycin compound according to claim 1 wherein Z is lower alkanoyl having 1–4 carbon atoms.

4. Mitomycin compounds according to claim 3, wherein Z is a member of the group consisting of formyl, acetyl, propionyl or butyryl.

5. Mitomycin compounds according to claim 1 wherein Z is a member of the group consisting of benzoyl, p-nitrobenzoyl or naphthoyl.

6. Mitomycin compounds according to claim 1 selected from the group consisting of:
7-demethoxy-6,7-dihydro-7-ethylenedioxymitomycin A,
7-demethoxy-6,7-dihydro-7-ethylenedioxymitomycin B,
7-demethoxy-6,7-dihydro-7-ethylenedioxymitomycin F,
7-demethoxy-6,7-dihydro-7-ethylenedioxymitomycin J,
6-chloro-7-demethoxy-6,7-dihydro-7-ethylenedioxymitomycin A,
6-chloro-7-demethoxy-6,7-dihydro-7-ethylenedioxymitomycin B, and
6-chloro-7-demethoxy-6,7-dihydro-7-ethylenedioxymitomycin F.

7. An antibacterial and anti-tumour pharmaceutical composition comprising a pharmacologically effective amount of a mitomycin compound according to claim 1.

* * * * *